(12) United States Patent
Katafuchi et al.

(10) Patent No.: US 7,351,318 B2
(45) Date of Patent: Apr. 1, 2008

(54) GAS SENSING ELEMENT

(75) Inventors: Toru Katafuchi, Kariya (JP); Keigo Mizutani, Okazaki (JP)

(73) Assignee: Denso Corporation (JP)

( * ) Notice: Subject to any disclaimer, the term of this patent is extended or adjusted under 35 U.S.C. 154(b) by 449 days.

(21) Appl. No.: 10/317,162

(22) Filed: Dec. 12, 2002

(65) Prior Publication Data

US 2003/0106795 A1 Jun. 12, 2003

(30) Foreign Application Priority Data

Dec. 12, 2001 (JP) .............................. 2001-378974

(51) Int. Cl.
*G01N 27/407* (2006.01)

(52) U.S. Cl. ..................... 204/425; 204/427; 73/23.31; 205/781

(58) Field of Classification Search ................ 204/425, 204/426, 427; 205/781; 73/23.31, 23.32
See application file for complete search history.

(56) References Cited

U.S. PATENT DOCUMENTS

| | | | |
|---|---|---|---|
| 5,866,799 A | 2/1999 | Kato et al. | |
| 5,985,118 A | 11/1999 | Makino et al. | |
| 6,071,393 A * | 6/2000 | Oshima et al. | 204/425 |
| 6,196,053 B1 | 3/2001 | Kato et al. | |
| 6,205,843 B1 | 3/2001 | Tanaka et al. | |
| 6,274,016 B1 * | 8/2001 | Hasei et al. | 204/424 |
| 6,332,965 B1 * | 12/2001 | Sugiyama et al. | 204/425 |
| 6,607,643 B2 | 8/2003 | Takahashi et al. | |
| 2001/0023823 A1 | 9/2001 | Takahashi et al. | |
| 2002/0038761 A1 | 4/2002 | Sugiyama et al. | |

FOREIGN PATENT DOCUMENTS

| | | |
|---|---|---|
| DE | 198 27 469 A1 * | 1/1999 |
| DE | 101 09 676 A1 * | 9/2001 |
| EP | 791825 | 8/1997 |
| EP | 798555 | 10/1997 |
| EP | 859233 | 8/1998 |
| EP | 928965 | 7/1999 |
| EP | 0987547 A2 | 3/2000 |
| EP | 1006354 A2 | 6/2000 |
| JP | 9-288086 | 11/1997 |
| JP | 9-318596 | 12/1997 |
| JP | 10-185868 | 7/1998 |
| JP | 10-227760 | 8/1998 |

(Continued)

OTHER PUBLICATIONS

Machine translation of JP 2000-121,604, Apr. 2000.*

(Continued)

*Primary Examiner*—Kaj K. Olsen
(74) *Attorney, Agent, or Firm*—Nixon & Vanderhye PC (57) ABSTRACT

A gas sensing element has at least a sensor cell consisting of a measured gas side electrode positioned in a measured gas chamber, a reference electrode being operative association with the measured gas side electrode, and a solid electrolytic substrate having surfaces on which the measured gas side electrode and the reference electrode are formed. The measured gas side electrode of the sensor cell contains at least one additive selected from the group consisting of Au, Ag, Cu, and Pb by an amount of 0.01 wt % to 2.0 wt % (external wt %) when an overall amount of the measured gas side electrode is 100 wt %.

6 Claims, 9 Drawing Sheets

FOREIGN PATENT DOCUMENTS

| | | |
|---|---|---|
| JP | 2885336 | 2/1999 |
| JP | 11-72477 | 3/1999 |
| JP | 11-183434 | 7/1999 |
| JP | 2000-121604 | 4/2000 |
| JP | 2000-230919 | 8/2000 |
| JP | 2001-318075 | 11/2001 |

OTHER PUBLICATIONS

Japanese Office Action dated Nov. 1, 2005 with translation.
Japanese Office Action dated Sep. 5, 2006 in Japanese Patent Application No. 2001-378974 together with English translation.

* cited by examiner

GAS SENSING ELEMENT

BACKGROUND OF THE INVENTION

This invention relates to a gas sensor installed in an exhaust passage or the like of an internal combustion engine to measure the concentration of NOx or a specific gas component contained in the exhaust gas.

To measure a NOx concentration, an oxygen concentration, or an air-fuel ratio in an engine combustion chamber, a gas sensor is generally installed in an exhaust system of an automotive engine. For example, the gas sensor includes a gas sensing element arranged in the following manner.

The gas sensing element includes a pump cell for pumping oxygen with respect to the measured gas chamber and a sensor cell for measuring the concentration of NOx introduced into the measured gas chamber.

The sensor cell, measuring the NOx concentration, includes a pair of sensor electrodes and a solid electrolytic substrate having surfaces on which the sensor electrodes are formed. One of the sensor electrodes is positioned in a measured gas chamber. The other sensor electrode is positioned in an air chamber into which the air is introduced as a reference gas. The sensor electrode exposed to a measured gas is made of a material having active nature against NOx.

Furthermore, the pump cell includes a pair of pump electrodes and a solid electrolytic substrate having surfaces on which the pump electrodes are formed. One of the pump electrodes is positioned in the measured gas chamber. The pump electrode exposed to the measured gas is made of a material having inactive nature against NOx.

The measurement of the NOx concentration in the sensor cell is performed based on an oxygen ion current generating due to decomposition of NOx on the measured gas side electrode. Accordingly, the oxygen concentration in the measured gas chamber must be very small or stationary.

To this end, the pump cell is used to adjust the oxygen concentration in the measured gas chamber. The pump electrode is necessarily provided to be exposed to the measured gas. Decomposition of NOx, if happens on the pump electrode, will give adverse influence to the measurement of NOx concentration at the sensor cell. The measured NOx concentration will be inaccurate in this case.

To solve this problem, a conventional method is to add an inactive additive, such as Au, to a Pt pump electrode of a pump cell. Alternatively, a conventional pump cell employs an alloy pump electrode. This is effective to suppress the decomposition of NOx.

A monitor cell may be provided adjacently to the measured gas chamber to monitor the oxygen concentration in the measured gas chamber. Decomposition of NOx, if happens on a monitor electrode, will give adverse influence to the measurement of NOx concentration at the sensor cell. The measured NOx concentration will be inaccurate in this case, too.

Hence, to solve this problem, a conventional monitor cell employs a Pt electrode containing an inactive additive, such as Au, or an alloy electrode. Using such an electrode makes it possible to suppress the decomposition of NOx.

However, when the gas sensing element is exposed to a high-temperature exhaust gas, Au components volatilize from the pump electrode or the monitor cell electrode and then deposit or adhere on the measured gas side electrode of the sensor cell. This causes a serious change in the properties of the measured gas side electrode and deteriorates the accuracy in the NOx concentration measurement.

SUMMARY OF THE INVENTION

In view of the above-described problems of the prior art, the present invention has an object to provide a gas sensing element which is capable of assuring long-lasting measuring accuracy.

In order to accomplish the above and other related objects, the present invention provides a gas sensing element including a measured gas chamber for storing a measured gas introduced from the outside, a pump cell, and a sensor cell. The pump cell includes first and second pump electrodes and a solid electrolytic substrate having surfaces on which the first and second pump electrodes are provided. The first pump electrode, positioned in the measures gas chamber, contains at least one additive selected from the group consisting of Au, Ag, Cu, and Pb. The second pump electrode is in operative association with the first pump electrode. The sensor cell includes a measured gas side electrode, a reference electrode, and a solid electrolytic substrate having surfaces on which the measured gas side electrode and the reference electrode are formed. The measured gas side electrode is provided in the measured gas chamber. The reference electrode is operative association with the measured gas side electrode. The measured gas side electrode of the sensor cell contains at least one additive selected from the group consisting of Au, Ag, Cu, and Pb by an amount of 0.01 wt % to 2.0 wt % (external wt %) when an overall amount of the measured gas side electrode is 100 wt %.

According to the gas sensing element of the present invention, the measured gas side electrode of the sensor cell contains a predetermined amount of additive selected from the group consisting of Au, Ag, Cu, and Pb.

If the additive selected from the group consisting of Au, Ag, Cu, and Pb is added to the electrode, the electrode will become inactive against a specific gas to be measured and the oxygen will be ionized. However, losing the strong activity makes the electrode suffer from the shortage of properties for decomposing the specific gas, such as NOx, into ions.

Au, Ag, Cu, and Pb volatilizing from the first pump electrode during the use of the gas sensing element may adhere or deposit on the measured gas side electrode of the sensor cell and deteriorate the properties of the sensor cell. Furthermore, according to a gas sensing element having a monitor cell, the above-described additive substances volatilize from a measured gas side electrode of a monitor cell and may adhere or deposit on the measured gas side electrode of the sensor cell.

Accordingly, adding a small amount of Au, Ag, Cu, or Pb to the measured gas side electrode of the sensor cell makes it possible to assure the long-lasting durability of the sensor cell (i.e., prevent the sensor properties from deteriorating) during the long life of the sensor cell.

As described above, according to the present invention, it becomes possible to provide a gas sensing element capable of maintaining excellent measuring accuracy during the life time of this sensing element.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Preferred embodiments of the present invention will be explained hereinafter with reference to attached drawings. Identical parts are denoted by the same reference numerals throughout the drawings.

First Embodiment

FIGS. 1 to 7 show a gas sensor in accordance with a first embodiment of the present invention.

The gas sensing element of this invention is a platelike multilayered element consisting of a plurality of solid electrolytic substrates or insulating substrates.

The gas sensing element includes a measured gas chamber into which the measured gas is introduced and an air chamber into which the air serving as a reference gas is introduced.

The pump cell is an electrochemical cell adapted for pumping (discharging or introducing) the oxygen with respect to the measured gas chamber.

The sensor cell is an electrochemical cell adapted to measure the concentration of a specific gas in the measured gas chamber. More specifically, the sensor cell measures the specific gas concentration based on an oxygen ion current occurring when the measured gas side electrode decomposes the specific gas contained in the measured gas. It is hence necessary for the measured gas side electrode to be active against the specific gas.

The pump electrode of the pump cell, positioned in the measured gas chamber, needs to be inactive and has insufficient or no capability for decomposing the specific gas contained in the measured gas.

Furthermore, it is possible to provide an O2 cell or an air-fuel ratio cell in addition to the pump cell and a sensor cell to measure the concentrations of a plurality or various kinds of gases simultaneously, so that the gas sensing element of this invention can be constituted as one of this kind of complex gas sensing elements. The O2 cell is an electrochemical cell capable of measuring the concentration of oxygen contained in the measured gas. The air-fuel ratio cell is an electrochemical cell capable of detecting a ratio of air to fuel in the combustion chamber of any kind of internal combustion engine, when the gas sensing element of the present invention is installed in an exhaust system of this internal combustion engine.

Regarding the measured gas side electrode of the sensor cell according to this invention, the content of Au, Ag, Cu, and Pb is in the range from 0.01 wt % to 2.0 wt % (external wt %) when an overall amount of the measured gas side electrode is 100 wt %.

If the content of this additive is less than 0.01 wt %, the additive component such as Au volatilized from the pump electrode of the pump cell will adhere or deposit on the measured gas side electrode. This will change the properties of the sensor cell and deteriorate the measuring accuracy. On the other hand, if the content of this additive is larger than 2.0 wt %, the activity of the measured gas side electrode will decline and it will become difficult to accurately measure the concentration of a specific gas.

According to this embodiment, it is preferable that a main component of the measured gas side electrode of the sensor cell is selected from the group consisting of Pt, Rh, Pd, Ir, and Ru.

The electrode containing the above-described substance or substances are active against NOx, CO, and HC, and accordingly the electrode decomposes the specific gas and produces oxygen ions which form an oxygen ion current. Thus, the electrode effectively detects the specific gas concentration based on the oxygen ion current thus produced.

Furthermore, the measured gas side electrode can be made of a material containing only one of the above-described components or can be made of a mixture or an alloy containing the above-described component or components.

Furthermore, according to this embodiment, it is preferable that the measured gas side electrode of the sensor cell contains at least one additive selected from the group consisting of Au, Ag, Cu, and Pb by an amount of 0.1 wt % to 1.0 wt % (external wt %) when an overall amount of the measured gas side electrode is 100 wt %.

According to this arrangement, even if the additive Au, Ag, Cu, and Pb adheres or deposits on the measured gas side electrode of the sensor cell, no substantial change occurs on the properties of the sensor cell and accordingly the measuring accuracy does not deteriorate.

If the content of this additive is less than 0.1 wt %, the properties of the sensor cell will change and the measuring accuracy will deteriorate. On the other hand, if the content of this additive is larger than 1.0 wt %, the activity of the measured gas side electrode will decline and it will become difficult to accurately measure the concentration of a specific gas.

Furthermore, according to this embodiment, it is preferable that the gas sensing element further includes an additional measured gas side electrode positioned in the measured gas chamber and containing at lease one additive selected from the group consisting of Au, Ag, Cu, and Pb, an additional reference electrode being operative association with the additional measured gas side electrode, and a monitor cell constituted by the additional measured gas side electrode, the additional reference electrode, and a solid electrolytic substrate having surfaces on which the additional measured gas side electrode and the additional reference electrode are formed.

With this arrangement, it becomes possible to monitor the oxygen concentration in the measured gas chamber. The oxygen concentration is used as a reference or standard in the control of operation of the pump cell. This enables the sensor cell to accurately detect the concentration of a specific gas such as NOx (refer to the first embodiment).

Furthermore, like the pump cell, the additional measured gas side electrode of the monitor cell is made of a material containing at least one additive selected from the group consisting of Au, Ag, Cu, and Pb. For example, an Au—Pt electrode is preferable as it is active against the specific gas, such as NOx, to be measured by the sensor cell. When the Au or other component adheres or deposits on the sensor cell, the activity of the electrode deteriorates with respect to the specific gas such as NOx.

Hereinafter, the practical examples of this embodiment will be explained with reference to the attached drawings.

Figure 1:
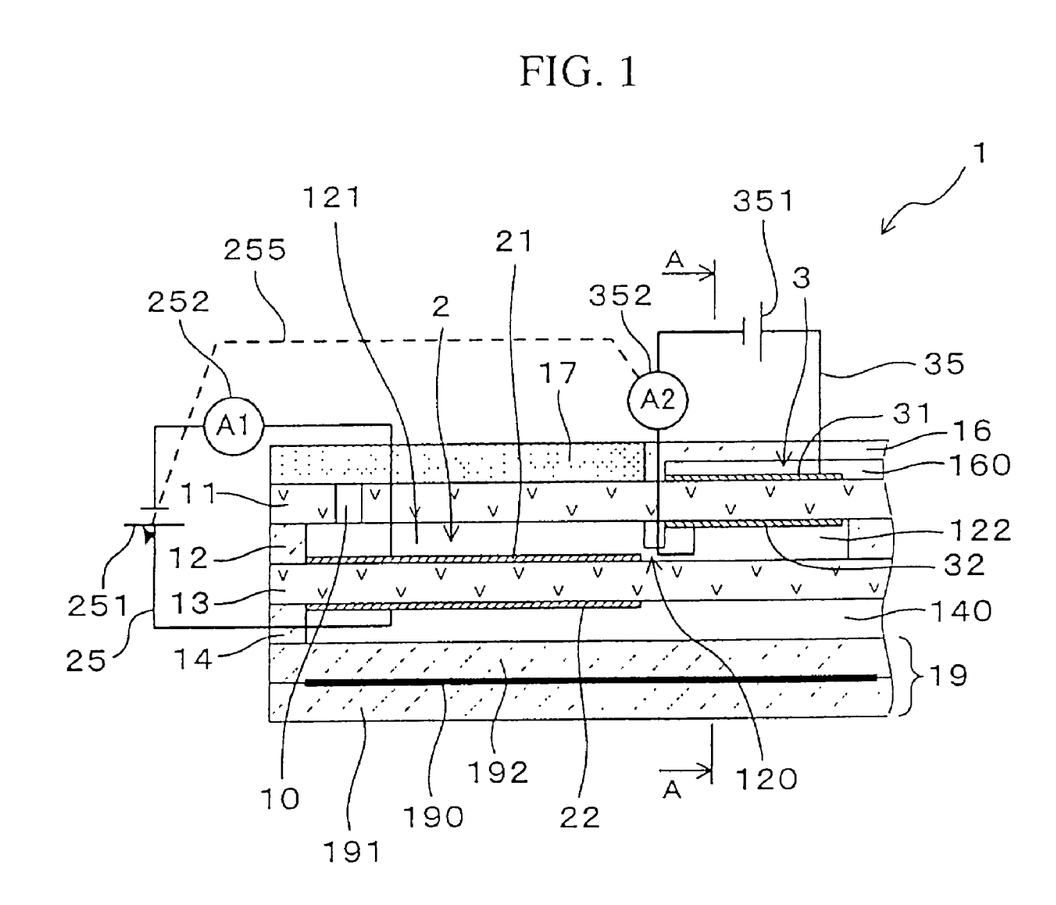
FIG. 1 is a cross-sectional diagram showing the arrangement of a gas sensing element in accordance with a first embodiment of the present invention.
Figure 2:
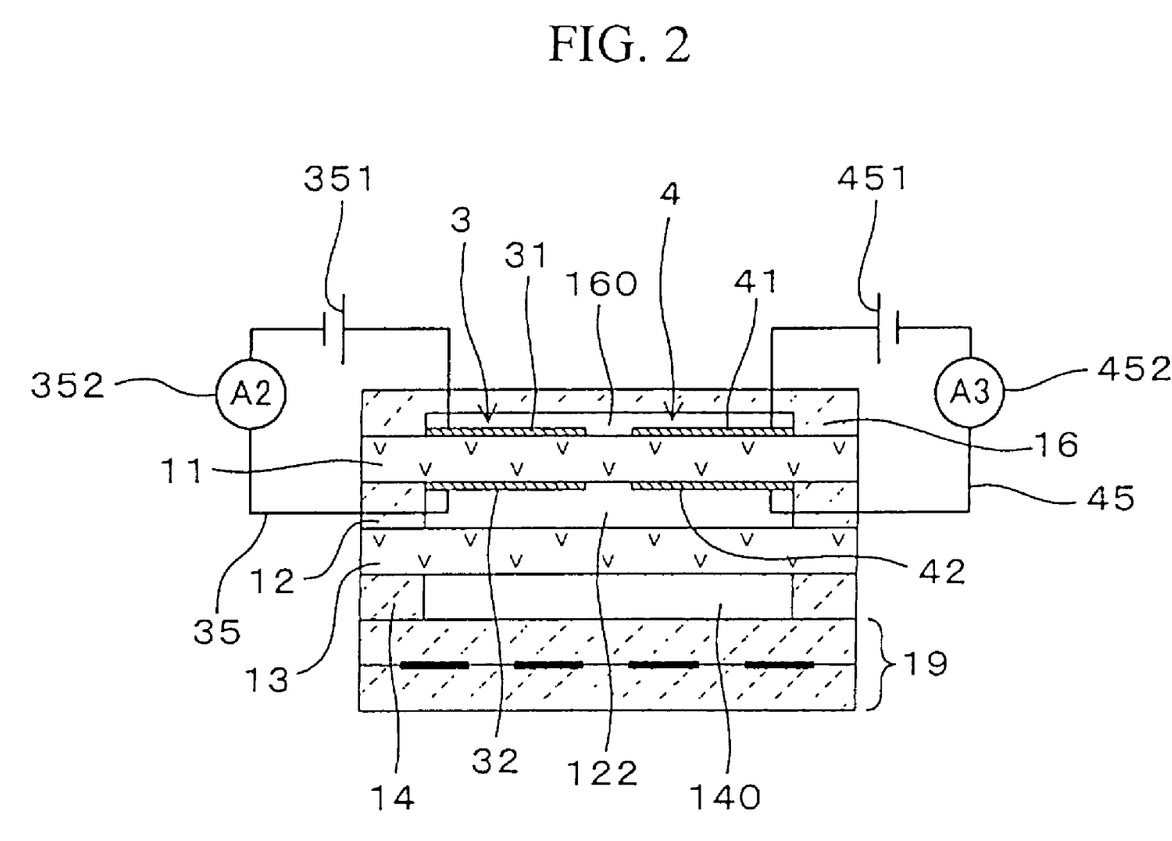
FIG. 2 is a transverse cross-sectional view showing the arrangement of the gas sensing element in accordance with the first embodiment of the present invention, taken along a line A-A shown in FIG. 1.

As shown in FIGS. 1 and 2, a gas sensing element 1 of the first embodiment includes a first measured gas chamber 121 storing a measured gas introduced from the outside, a first pump electrode 21 provided in the first measured gas chamber 121 and containing Au, and a second pump electrode 22 being in operative association with the first pump electrode 21. The first pump electrode 21 and the second pump electrode 22 are provided on opposite surfaces of a second solid electrolytic substrate 13. The first pump electrode 21, the second pump electrode 22, and the second solid electrolytic substrate 13 cooperatively constitute a pump cell 2.

Furthermore, the gas sensing element 1 of this embodiment includes a measured gas side electrode 42 positioned in a second measured gas chamber 122, and a reference electrode 41 being operative association with the measured gas side electrode 42. The reference electrode 41 and the measured gas side electrode 42 are provided on opposite surfaces of a first solid electrolytic substrate 11. The measured gas side electrode 42, the reference electrode 41, and the first solid electrolytic substrate 11 cooperatively constitute a sensor cell 4.

The measured gas side electrode 42 of sensor cell 4 contains Au by an amount of 0.2 wt % (external wt %) when the overall amount of the measured gas side electrode is 100 wt %.

Hereinafter, the first embodiment will be explained in more detail.

As shown in FIGS. 1 and 2, the gas sensing element 1 of this embodiment has a multilayered body including the first solid electrolytic substrate 11, a spacer 12 defining the measured gas chamber, the second solid electrolytic substrate 13, a spacer 14 defining an air chamber, and a ceramic heater 19.

The gas sensing element 1 includes the first measured gas chamber 121, the second measured gas chamber 122 in addition to a first air chamber 140 and a second air chamber 160. The pump cell 2 is provided for pumping the oxygen with respect to the first measured gas chamber 121. A monitor cell 3 monitors the oxygen concentration in the second measured gas chamber 122. The sensor cell 4 detects the NOx concentration in the second measured gas chamber 122.

The first measured gas chamber 121 and the second measured gas chamber 122, both being defined in the spacer 12, are interposed between the first solid electrolytic substrate 11 and the second solid electrolytic substrate 13. The first solid electrolytic substrate 11 has a through-hole 10 extending vertically across this body and allowing the first measured gas chamber 121 to communicate with the outside. The first measured gas chamber 121 and the second measured gas chamber 122 communicate with each other via a diffusion passage 120 extending along an upper surface of the second solid electrolytic substrate 13.

Furthermore, the gas sensing element 1 of this embodiment includes a porous diffusion layer 17 covering the outer opening of the through-hole 10 of the first solid electrolytic substrate 11. A spacer 16, provided next to the porous diffusion layer 17, defines the second air chamber 160 underlying this spacer 16. Furthermore, the first air chamber 140 defined in the spacer 14 is interposed between the second solid electrolytic substrate 13 and the ceramic heater 19. The air, serving as a reference gas, is introduced into the first air chamber 140.

The ceramic heater 1 consists of a heater substrate 191, a heat-generating element 190 mounted on the heater substrate 191, and a coating substrate 192 covering the heat-generating element 190.

The material for the above-described first and second solid electrolytic substrates 11 and 13 is zirconia ceramic. On the other hand, the material for the remaining substrates is alumina ceramic.

The pump cell 2 includes the first pump electrode 21 and the second pump electrode 22 provided on the opposite surfaces of the second solid electrolytic substrate 13. The first pump electrode 21 is positioned in the first measured gas chamber 121. The second pump electrode 22 is positioned in the first air chamber 140. A pump circuit 25, including a power source 251 and an ammeter 252, is connected between the first pump electrode 21 and the second pump electrode 22.

The monitor cell 3 includes a measured gas side electrode 32 and the reference electrode 31 provided on the opposite surfaces of the first solid electrolytic substrate 11. The measured gas side electrode 32 is positioned in the second measured gas chamber 122. The reference electrode 31 is positioned in the second air chamber 160. A monitor circuit 35, including a power source 351 and an ammeter 352, is connected between the measured gas side electrode 32 and the reference electrode 31.

The sensor cell 4 includes a measured gas side electrode 42 and the reference electrode 41 provided on the opposite surfaces of the first solid electrolytic substrate 11. The measured gas side electrode 42 is positioned in the second measured gas chamber 122. The reference electrode 41 is positioned in the second air chamber 160. A sensor circuit 45, including a power source 451 and an ammeter 452, is connected between the measured gas side electrode 42 and the reference electrode 41.

A feedback circuit 255 is provided to control the operation of the pump cell 2 based on the signal of the monitor cell 3.

More specifically, the power source 251 in the pump circuit 25 is feedback controlled based on the current signal detected by the ammeter 352 in the monitor circuit 35.

Each of the first pump electrode 21 and the measured gas side electrode 32 is a Pt—Au electrode having inactive nature against NOx and contains Au by an amount of 3 wt %. The measured gas side electrode 42 is a Pt—Rh electrode having active nature against NOx. The remaining electrodes 22, 31, and 41 are Pt—Rh electrodes, respectively. The Pt—Rh electrode contains Rh by an amount of 20 wt %. The measured gas side electrode 42 contains Au by an amount of 0.2 wt %.

According to the gas sensing element 1 of this embodiment, the measured gas side electrode 42 of the sensor cell 4 contains a predetermined amount of Au component. During the use of the gas sensing element 1, Au components volatilize from the first pump electrode 21 of the pump cell 2 and from the measured gas side electrode 32 of the monitor cell 3. The volatilized Au components adhere or deposit on the measured gas side electrode 42 of the sensor cell 4. Even in such a case, the properties of sensor cell 4 do not change. The measuring accuracy is always maintained at satisfactory levels.

As described above, the first embodiment provides a gas sensing element capable of assuring long-lasting measuring accuracy.

The first embodiment of the present invention shows the test result with respect to Au contents (i.e., Au deposit amount), electrode activation, and the voltage-current characteristics of the gas sensing element.

First of all, gas sensing elements having the same arrangement as that of the first embodiment, are prepared for this test. In each of the prepared gas sensing elements, no Au component is contained in each of a measured gas side electrode of the sensor cell. A gas sensor, incorporating the prepared gas sensing element, was installed in the exhaust gas system of a practical automotive engine to measure the electrode activity through an endurance test performed on this practical automotive engine running a predetermined endurance distance.

The endurance distance in this test is a converted value of a driving time of the tested engine and is equivalent to an actual traveling distance of an automotive vehicle installing this engine.

Figure 6:
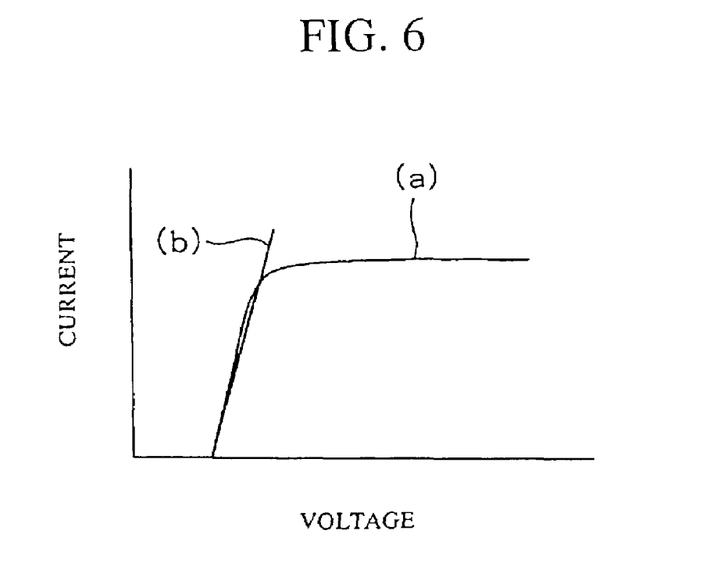
FIG. 6 is a graph showing a relationship between the voltage and the current in accordance with the first embodiment of the present invention.

FIG. 6 shows a current value flowing across the sensor cell which is monitored by applying a voltage which takes various values. In FIG. 6, an abscissa represents the voltage value and an ordinate represents the current value. As shown in FIG. 6, the linear characteristics is observed in a certain voltage region (i.e., 0.2V~0.4V). In FIG. 6, the line (a) represents the relationship between the voltage and the current. The line (b) represents an inclination in the voltage region from 0.2V to 0.4V.

When the inclination of the line (b) is large, the electric resistance is small. NOx decomposes at a lower voltage. The electrode can be evaluated as having a highly activated condition. Thus, it is possible to measure the electrode activation by plotting on a map the relationship between the voltage and the current obtained from the above-described method.

Figure 3:
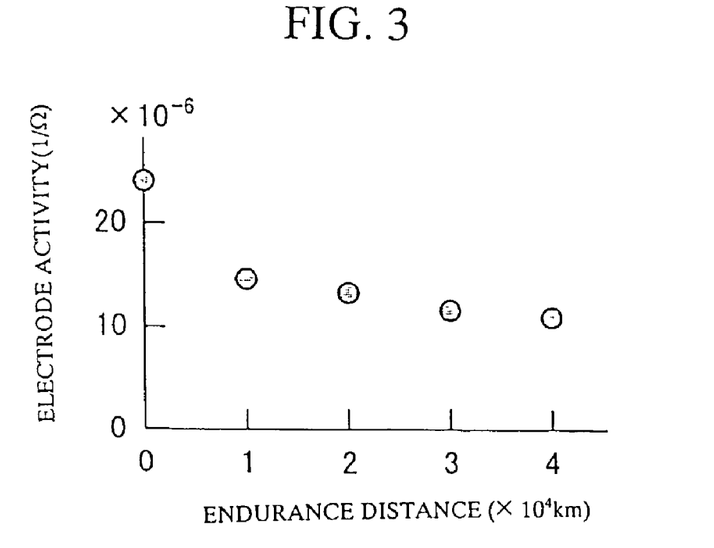
FIG. 3 is a graph showing a relationship between the endurance distance and electrode activity in accordance with the first embodiment of the present invention.

FIG. 3 shows the measurement result. As shown in this drawing, it is understood that the electrode activity declines greatly in the beginning of the endurance test.

Figure 4:
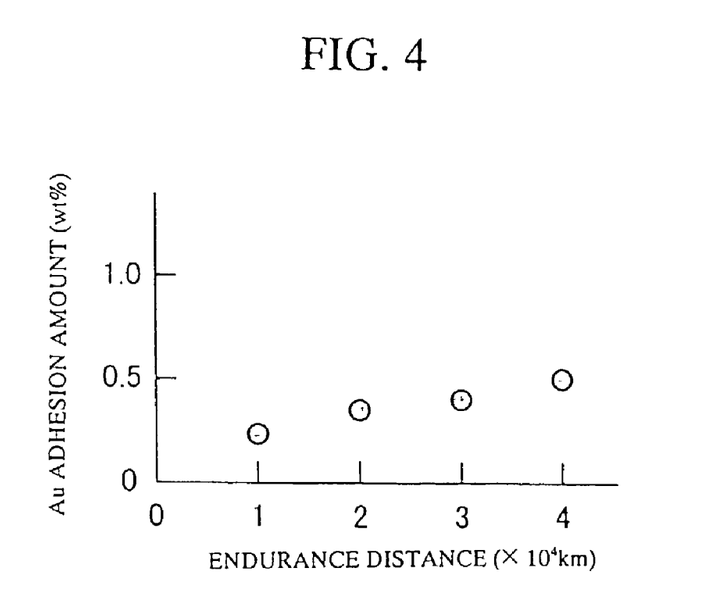
FIG. 4 is a graph showing a relationship between the endurance distance and the Au deposit amount in accordance with the first embodiment of the present invention.

Meanwhile, the Au amount deposit on the measured gas side electrode in this test was measured. Regarding the method for measuring the impurity amount, conventionally known are XPS, EPMA and others. As EPMA is superior to others in the measuring depth, the method employed in this test for measuring the Au deposit amount was EPMA. FIG. 4 shows the measurement result. As shown in this drawing, the Au deposit amount gradually increases with increasing endurance distance.

Figure 5:
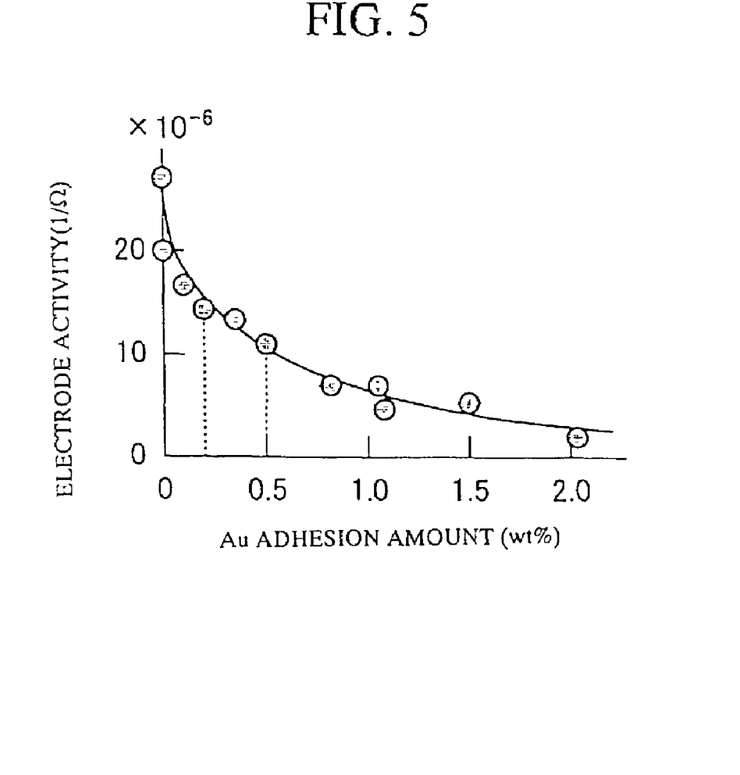
FIG. 5 is a graph showing a relationship between the Au deposit amount and electrode activity in accordance with the first embodiment of the present invention.

Using the measurement results shown in FIGS. 3 and 4, the relationship between the Au deposit amount and the electrode activity can be derived as shown in FIG. 5. As apparent from FIG. 5, the electrode activity declines with increasing Au deposit amount. The decline of electrode activity is steep in the beginning but is moderate in the later stage.

Then, the following two, first and second, gas sensing elements were prepared for a comparison. The first gas sensing element has the arrangement shown in the first embodiment and contains no Au in the measured gas side electrode. The second gas sensing element has the arrangement shown in the first embodiment but contains Au by an amount of 0.2 wt % in the measured gas side electrode. These first and second gas sensing elements were subjected to the endurance test similar to that explained with reference to FIGS. 3 and 4. The output current of the sensor cell was measured in the atmosphere containing 1,000 ppm of NOx before and after the endurance test thus performed, to obtain an output change rate expressed by the following formula.

{(pre-test output)−(post-test output)}/(pre-test output)×100

Figure 7:
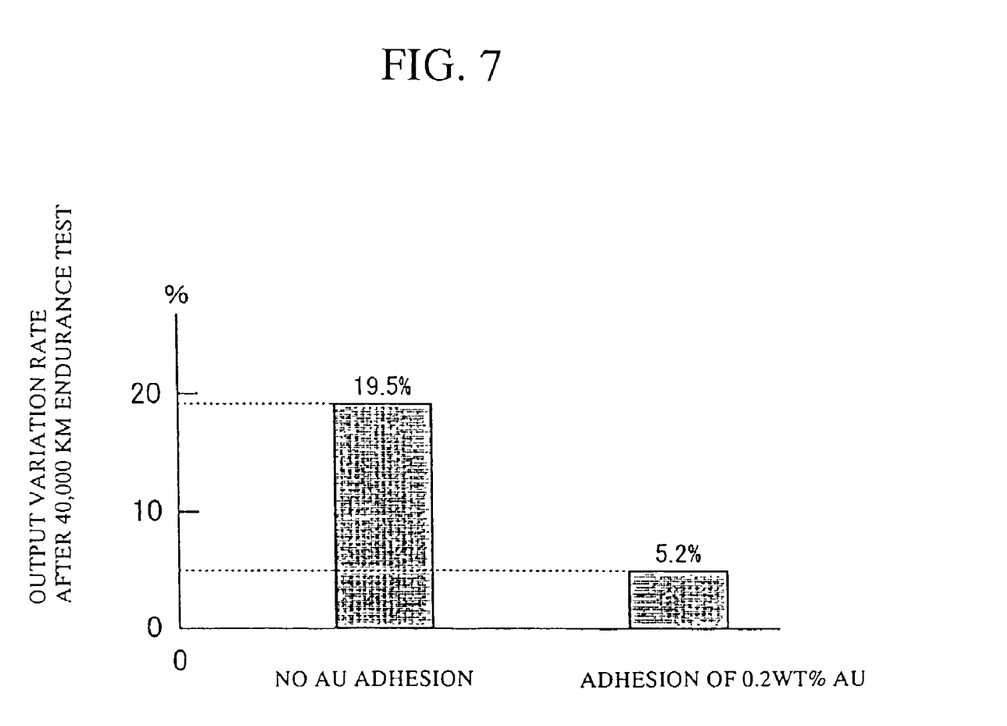
FIG. 7 is a graph showing the comparison of output changes between a gas sensing element having a measured gas side electrode containing no Au and a gas sensing element having a measured gas side electrode containing Au.

FIG. 7 shows the output change rate thus obtained.

As understood from FIG. 7, the output change rate greatly depends on the presence of Au components. Adding Au of 0.2 wt % brings the effect of greatly reducing the output change rate.

In other words, adding an Au additive brings the effect of stabilizing the sensor output.

Second Embodiment

Figure 8:
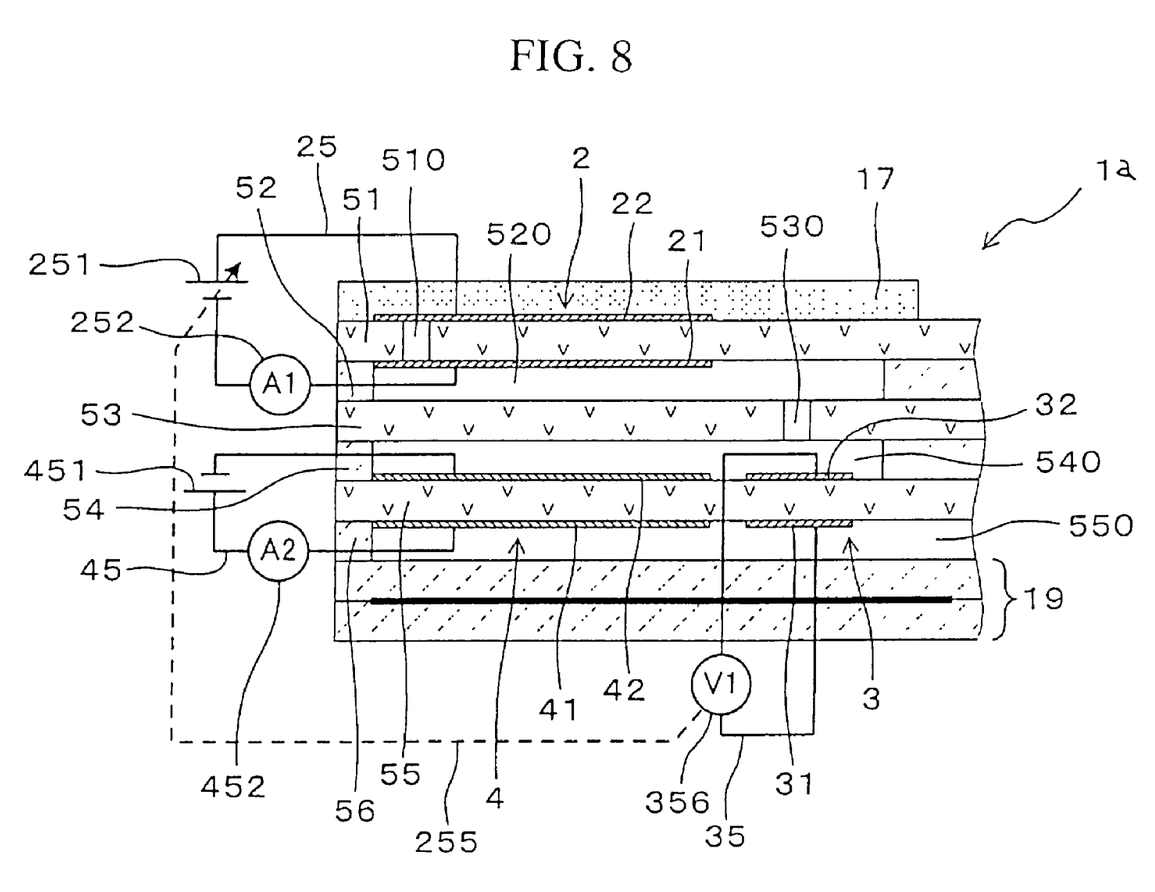
FIG. 8 is a cross-sectional diagram showing the arrangement of a gas sensing element in accordance with a second embodiment of the present invention, according to which two measuring gas chambers are offset from each other in the direction normal to the surfaces of multilayered substrates.

FIG. 8 shows a gas sensing element in accordance with a second embodiment of the present invention. According to the second embodiment, a first measured gas chamber 520 and a second measured gas chamber 540 are offset from each other in the direction normal to the surfaces of multilayered substrates including solid electrolytic substrates 51 to 55.

A gas sensing element 1a of this embodiment has a multilayered body consisting of a first solid electrolytic substrate 51, a first spacer 52, a second solid electrolytic substrate 53, a second spacer 54, a third solid electrolytic substrate 55, a third spacer 56, and a ceramic heater 19.

The first spacer 52 defines the first measured gas chamber 520 interposed between the first solid electrolytic substrate 51 and the second solid electrolytic substrate 53. Similarly, the second spacer 54 defines the second measured gas chamber 540 interposed between the second solid electrolytic substrate 53 and the third solid electrolytic substrate 55. The third spacer 56 defines an air chamber 550 interposed between the third solid electrolytic substrate 55 and the ceramic heater 19.

The first solid electrolytic substrate 51 has a through-hole 510 extending vertically across this body, through which a measured gas is introduced into the first measured gas chamber 520. A porous diffusion layer 17 is accumulated on the first solid electrolytic substrate 51 so as to cover the outer opening of the through-hole 510. The first measured gas chamber 520 and the second measured gas chamber 540 communicate with each other via a diffusion passage 530 extending vertically across the second solid electrolytic substrate 53.

A pump cell 2 has a first pump electrode 21 positioned in the first measured gas chamber 520 and a second pump electrode 22 exposed to the outer atmosphere via the porous diffusion layer 17. The first pump electrode 21 and the second pump electrode 22 are provided on opposite surfaces of the first solid electrolytic substrate 51.

The sensor cell 4 has a measured gas side electrode 42 positioned in the second measured gas chamber 540 and a reference electrode 41 positioned in the air chamber 550. The measured gas side electrode 42 and the reference electrode 41 are provided on opposite surfaces of the third solid electrolytic substrate 55. The monitor cell 3 has a measured gas side electrode 32 positioned in the second measured gas chamber 540 and a reference electrode 31 positioned in the air chamber 550. The measured gas side electrode 32 and the reference electrode 31 are provided on opposite surfaces of the third solid electrolytic substrate 55.

A pump circuit 25, including a power source 251 and an ammeter 252, is connected between the first pump electrode 21 and the second pump electrode 22 of the pump cell 2. A monitor circuit 35, including a voltmeter 356, is connected between the reference electrode 31 and the measured gas side electrode 32 of the monitor cell 3. A sensor circuit 45, including a power source 451 and an ammeter 452, is connected between the reference electrode 41 and the measured gas side electrode 42 of the sensor cell 4.

Furthermore, a feedback circuit 255 is provided to control the operation of the pump cell 2 based on the signal of the monitor cell 3. More specifically, the power source 251 in the pump circuit 25 is feedback controlled based on the voltage signal detected by the voltmeter 356 in the monitor circuit 35.

Each of the first pump electrode 21 and the measured gas side electrode 32 is a Pt—Au electrode having inactive nature against NOx. The measured gas side electrode 42 is a Pt—Rh electrode having active nature against NOx. The remaining electrodes 22, 31, and 41 are Pt—Rh electrodes, respectively. The measured gas side electrode 42 contains Au by an amount of 0.2 wt %. The rest of the arrangement of this embodiment is similar to that of the first embodiment. Thus, the functions and effects of the first embodiment can be also obtained by this embodiment.

Figure 9:
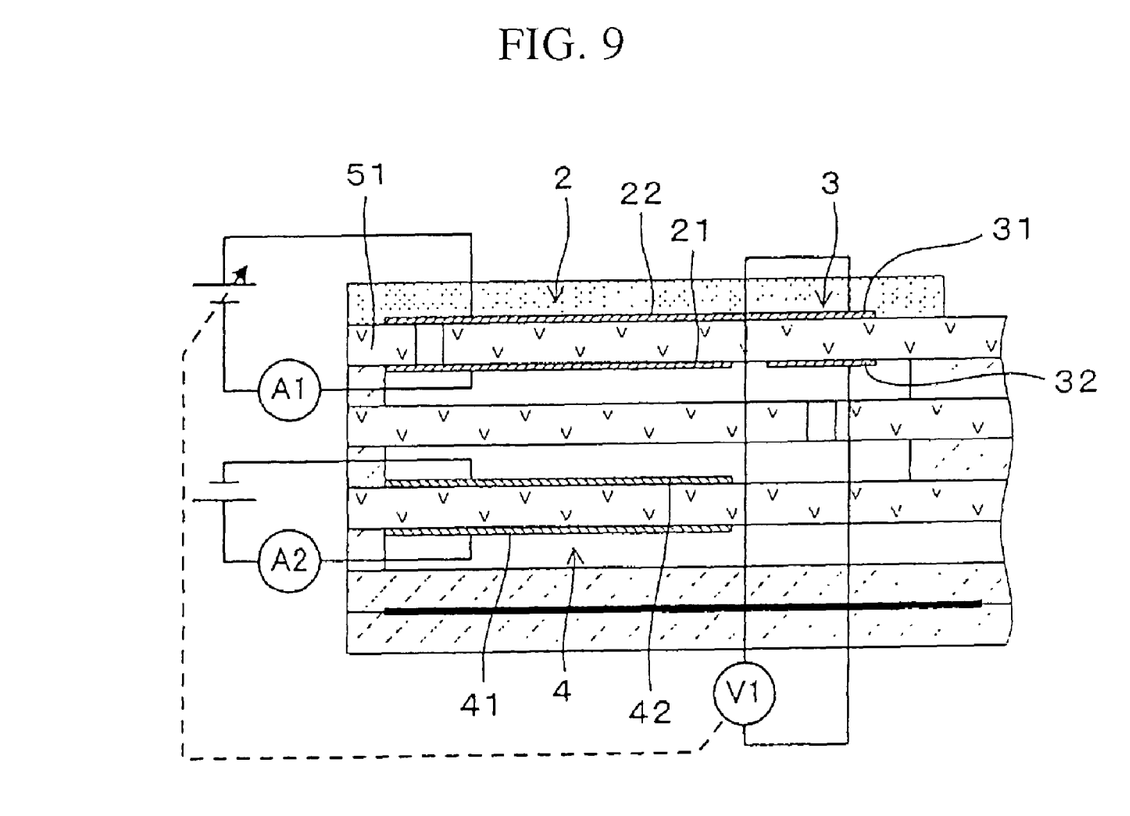
FIG. 9 is a cross-sectional diagram showing the arrangement of another gas sensing element in accordance with the second embodiment of the present invention, according to which two measuring gas chambers are offset from each other in the direction normal to the surfaces of multilayered substrates but the overall arrangement is arranged differently from that shown in FIG. 8.

Alternatively, as shown in FIG. 9, it is possible to provide the monitor cell 3 on the first solid electrolytic substrate 51. In this case, it is possible to integrate the second pump electrode 22 of the pump cell 2 with the reference electrode 31 of the monitor cell 3.

Third Embodiment

Figure 10:
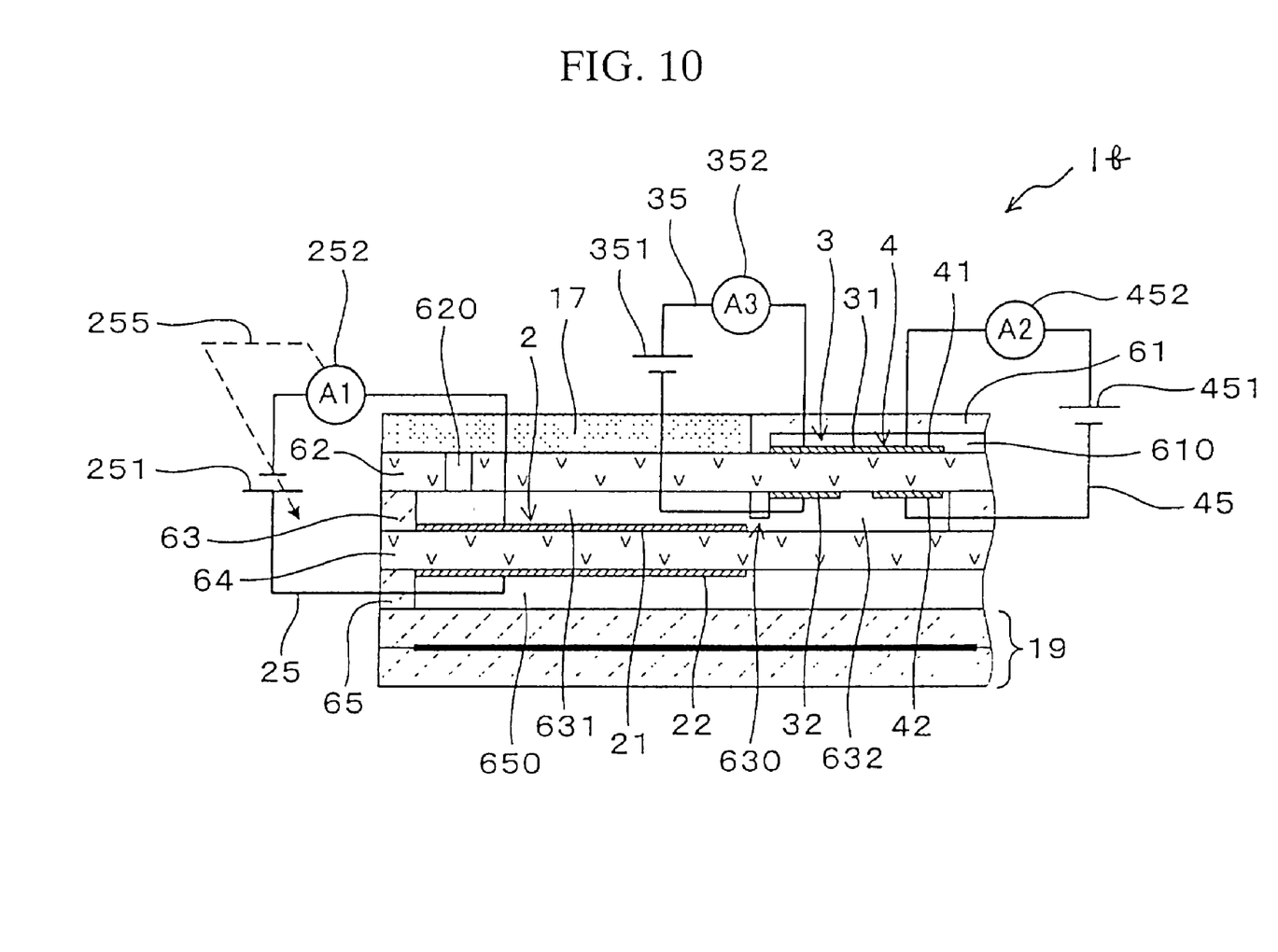
FIG. 10 is a cross-sectional diagram showing the arrangement of a gas sensing element in accordance with a third embodiment of the present invention, according to which a monitor cell and a sensor cell are serially arranged.

FIG. 10 shows a gas sensing element in accordance with a third embodiment of the present invention. According to the third embodiment, as shown in FIG. 10, a sensor cell 4 and a monitor cell 3 are serially or adjacently connected.

The gas sensing element 1b of this embodiment has a multilayered body consisting of a first spacer 61, a first solid electrolytic substrate 62, a second spacer 63, a second solid electrolytic substrate 64, a third spacer 65, and a ceramic heater 19.

The first spacer 61 defines a first air chamber 610 underlying this spacer along an upper surface of the first solid electrolytic substrate 62. The second spacer 63 defines a first measured gas chamber 631 and a second measured gas chamber 632 interposed between the first solid electrolytic substrate 62 and the second solid electrolytic substrate 64. Similarly, the third spacer 65 defines a second air chamber 650 interposed between the second solid electrolytic substrate 64 and the ceramic heater 19.

The first solid electrolytic substrate 62 has a through-hole 620 extending vertically across its body, through which a measured gas is introduced into the first measured gas chamber 631. A porous diffusion layer 17 is accumulated on the first solid electrolytic substrate 62 so as to cover the outer opening of the through-hole 620. The first measured gas chamber 631 and the second measured gas chamber 632 communicate with each other via a diffusion passage 630 extending along an upper surface of the second solid electrolytic substrate 64.

A pump cell 2 has a first pump electrode 21 positioned in the first measured gas chamber 631 and a second pump electrode 22 positioned in the second air chamber 650. The first pump electrode 21 and the second pump electrode 22 are provided on opposite surfaces of the second solid electrolytic substrate 64.

The sensor cell 4 has a measured gas side electrode 42 positioned in the second measured gas chamber 632 and a reference electrode 41 positioned in the first air chamber 610. The measured gas side electrode 42 and the reference electrode 41 are provided on opposite surfaces of the first solid electrolytic substrate 62. The monitor cell 3 has a measured gas side electrode 32 positioned in the second measured gas chamber 632 and a reference electrode 31 positioned in the first air chamber 610. The measured gas side electrode 32 and the reference electrode 31 are provided on opposite surfaces of the first solid electrolytic substrate 62.

A pump circuit 25, including a power source 251 and an ammeter 252, is connected between the first pump electrode 21 and the second pump electrode 22 of the pump cell 2. A monitor circuit 35, including a power source 351 and an ammeter 352, is connected between the reference electrode 31 and the measured gas side electrode 32 of the monitor cell 3. A sensor circuit 45, including a power source 451 and an ammeter 452, is connected between the reference electrode 41 and the measured gas side electrode 42 of the sensor cell 4.

Furthermore, a feedback circuit 255 is provided to control the operation of the pump cell 2. More specifically, the power source 251 in the pump circuit 25 is feedback controlled based on the current signal detected by the ammeter 252 in the pump circuit 25.

Each of the first pump electrode 21 and the measured gas side electrode 32 is a Pt—Au electrode having inactive nature against NOx. The measured gas side electrode 42 is a Pt—Rh electrode having active nature against NOx. The remaining electrodes 22, 31, and 41 are Pt—Rh electrodes, respectively. The measured gas side electrode 42 contains Au by an amount of 0.2 wt %.

The rest of the arrangement of this embodiment is similar to that of the first embodiment. Thus, the functions and effects of the first embodiment can be also obtained by this embodiment.

Besides the disclosed arrangement, it is possible to provide the pump cell 2 on the solid electrolytic substrate 62 and provide the sensor cell 4 and the monitor cell 3 on the solid electrolytic substrate 64.

Fourth Embodiment

Figure 11:
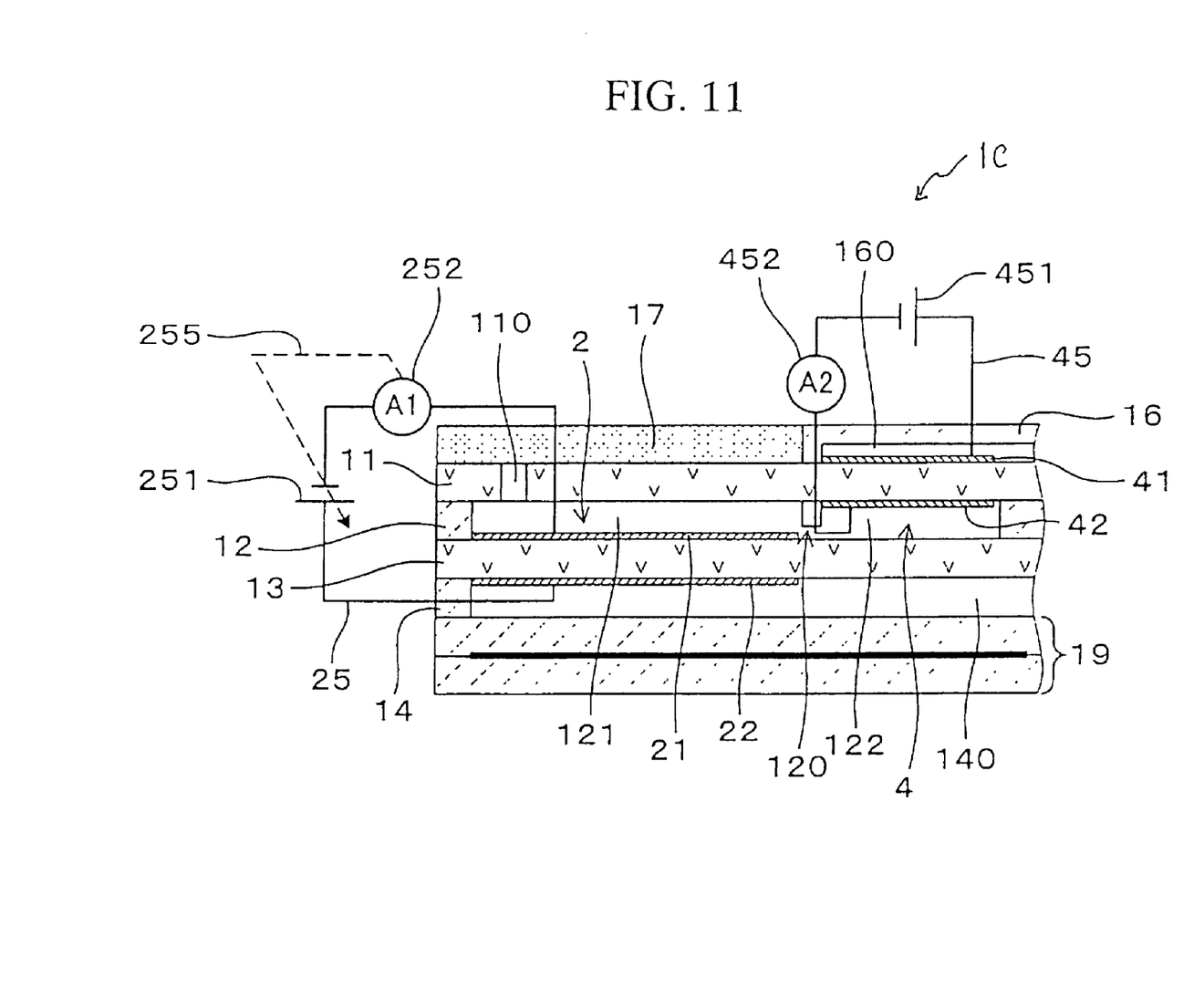
FIG. 11 is a cross-sectional diagram showing the arrangement of a gas sensing element in accordance with a third embodiment of the present invention, which includes only the sensor cell and the pump cell.

FIG. 11 is a gas sensing element in accordance with a fourth embodiment of the present invention which is structurally similar to the fist embodiment but is different in that it is a two-cell type gas sensing element 1c having no monitor cell.

According to the gas sensing element 1c of the fourth embodiment, a feedback circuit 255 is provided to feedback control the power source 251 in the pump circuit 25 based on the current signal detected by the ammeter 252 in the pump circuit 25.

The rest of the arrangement of this embodiment is similar to that of the first embodiment. Thus, the functions and effects of the first embodiment can be also obtained by this embodiment.

Besides the disclosed arrangement, it is possible to provide the pump cell 2 on the solid electrolytic substrate 62 and provide the sensor cell 4 and the monitor cell 3 on the solid electrolytic substrate 64.

What is claimed is:

1. A gas sensing element comprising,
   a measured gas chamber for storing a measured gas introduced from an outside of the element;
   a reference gas chamber for storing a reference gas;
   a first pump electrode positioned in said measured gas chamber and containing Au;
   a second pump electrode being in operative association with said first pump electrode;
   a pump cell constituted by said first and second pump electrodes and a solid electrolytic substrate having surfaces on which said first and second pump electrodes are provided;
   a measured gas side electrode positioned in said measured gas chamber;
   a reference electrode positioned in said reference gas chamber so as to be operatively associated with said measured gas side electrode;
   a sensor cell constituted by said measured gas side electrode, said reference electrode, and a solid electrolytic substrate having surfaces on which said measured gas side electrode and said reference electrode are formed; and
   a sensor circuit for detecting a concentration of NOx included in the measured gas from an electric current output from said sensor cell,
   wherein said sensor circuit gives a difference in a sensing voltage between said measured gas side electrode and said reference electrode of said sensor cell to decompose NOx of the measured gas on the measured gas side electrode and to generate an oxygen ion current in said solid electrolytic substrate due to decomposition of the NOx, and measures the electric current generated from the oxygen ion current to detect the concentration of NOx said measured gas side electrode of said sensor cell is mainly made of Pt and Rh, and said measured gas side electrode contains Au by an amount of 0.01 wt % to 2.0 wt % (external wt %) when an overall amount of said measured gas side electrode of said sensor cell is 100 wt %.

2. The gas sensing element in accordance with claim 1, wherein said measured gas side electrode of said sensor cell contains Au by an amount of 0.01 wt % to 1.0 wt % (external wt %) when an overall amount of said measured gas side electrode of said sensor cell is 100 wt %.

3. The gas sensing element in accordance with claim 1, further comprising
   an additional measured gas side electrode positioned in said measured gas chamber and containing at least one additive selected from the group consisting of Au, Ag, Cu, and Pb,
   an additional reference electrode being operative association with said additional measured gas side electrode, and
   a monitor cell constituted by said additional measured gas side electrode, said additional reference electrode, and a solid electrolytic substrate having surfaces on which said additional measured gas side electrode and said additional reference electrode are formed.

4. The gas sensing element in accordance with claim 1, wherein said measured gas side electrode of said sensor cell contains Rh by an amount of almost 20 wt %.

5. The gas sensing element in accordance with claim 1, wherein said measured gas side electrode of said sensor cell contains Au by an amount of almost 0.2 wt %.

6. The gas sensing element in accordance with claim 1, wherein the pump cell is adapted to discharge or introduce oxygen from or into the measured gas of said measured gas chamber.

* * * * *